(12) United States Patent
Ignagni et al.

(10) Patent No.: US 7,840,270 B2
(45) Date of Patent: Nov. 23, 2010

(54) SYSTEM AND METHOD FOR CONDITIONING A DIAPHRAGM OF A PATIENT

(75) Inventors: Anthony R. Ignagni, Oberlin, OH (US); Raymond P. Onders, Shaker Heights, OH (US)

(73) Assignee: Synapse Biomedical, Inc., Oberlin, OH (US)

( * ) Notice: Subject to any disclaimer, the term of this patent is extended or adjusted under 35 U.S.C. 154(b) by 1535 days.

(21) Appl. No.: 10/897,685

(22) Filed: Jul. 23, 2004

(65) Prior Publication Data

US 2005/0021102 A1 Jan. 27, 2005

Related U.S. Application Data

(60) Provisional application No. 60/481,124, filed on Jul. 23, 2003.

(51) Int. Cl.
*A61N 1/18* (2006.01)

(52) U.S. Cl. .......................................... 607/42; 600/529

(58) Field of Classification Search .................. 607/42; 600/52, 529
See application file for complete search history.

(56) References Cited

U.S. PATENT DOCUMENTS

| | | | |
|---|---|---|---|
| 1,693,734 A | 12/1928 | Waggoner et al. | |
| 2,532,788 A | 12/1950 | Sarnoff | |
| 2,664,880 A | 1/1954 | Wales | |
| 4,699,875 A | 10/1987 | Appel | |
| 4,827,935 A | 5/1989 | Geddes et al. | |
| 4,830,008 A * | 5/1989 | Meer | 607/42 |
| 4,989,617 A | 2/1991 | Memberg et al. | |
| 5,056,519 A | 10/1991 | Vince | |
| 5,314,463 A | 5/1994 | Camps et al. | |
| 5,368,035 A | 11/1994 | Hamm et al. | |
| 5,429,636 A | 7/1995 | Shikhman et al. | |
| 5,472,438 A | 12/1995 | Schmit et al. | |
| 5,524,632 A | 6/1996 | Stein et al. | |
| 5,527,358 A | 6/1996 | Mehmanesh et al. | |
| 5,678,535 A | 10/1997 | DiMarco | |
| 5,716,392 A | 2/1998 | Bourgeois et al. | |
| 5,718,248 A | 2/1998 | Trumble et al. | |

(Continued)

FOREIGN PATENT DOCUMENTS

| | | |
|---|---|---|
| EP | 996482 A1 | 5/2000 |
| EP | 873155 B1 | 6/2003 |
| EP | 1653863 A2 | 5/2006 |
| EP | 1660177 A1 | 5/2006 |
| EP | 1393773 B1 | 10/2006 |
| EP | 1306104 B1 | 1/2007 |
| EP | 1205202 B1 | 6/2007 |
| WO | WO86/00234 | 1/1986 |

OTHER PUBLICATIONS

DiMarco et al. "Phrenic Nerve Pacing in a Tetraplegic Patient via Intramuscular Diaphragm Electrodes." American Journal of Respiratory and Critical Care Medicine Dec. 15, 2002; 166(12 Pt 1): 1604-1606.*

(Continued)

*Primary Examiner*—Scott M Getzow
*Assistant Examiner*—Joseph M Dietrich
(74) *Attorney, Agent, or Firm*—Shay Glenn LLP

(57) ABSTRACT

A method of conditioning a diaphragm of a patient is provided. The method can include the steps of implanting an electrode adjacent a target site in the diaphragm of the patient and operating the electrode to deliver a sufficient amount of electrical stimulation to the target site in the diaphragm of the patient to cause the diaphragm to contract.

14 Claims, 5 Drawing Sheets

U.S. PATENT DOCUMENTS

| | | | |
|---|---|---|---|
| 5,792,165 | A | 8/1998 | Klieman et al. |
| 5,797,923 | A | 8/1998 | Aiyar et al. |
| 5,813,399 | A * | 9/1998 | Isaza et al. ............ 128/204.21 |
| 5,814,086 | A | 9/1998 | Hirschberg et al. |
| 5,849,290 | A | 12/1998 | Brown et al. |
| 5,851,783 | A | 12/1998 | Appel et al. |
| 6,035,856 | A | 3/2000 | LaFontaine et al. |
| 6,194,217 | B1 | 2/2001 | Matson |
| 6,198,970 | B1 * | 3/2001 | Freed et al. .................. 607/42 |
| 6,210,970 | B1 | 4/2001 | Matson |
| 6,245,053 | B1 | 6/2001 | Benjamin |
| 6,311,692 | B1 | 11/2001 | Vaska et al. |
| 6,321,109 | B2 | 11/2001 | Ben-Haim et al. |
| 6,360,740 | B1 | 3/2002 | Ward et al. |
| 6,397,108 | B1 | 5/2002 | Camps et al. |
| 6,405,732 | B1 | 6/2002 | Edwards et al. |
| 6,415,183 | B1 | 7/2002 | Scheiner et al. |
| 6,463,327 | B1 * | 10/2002 | Lurie et al. .................. 607/42 |
| 6,477,423 | B1 | 11/2002 | Jenkins |
| 6,571,127 | B1 | 5/2003 | Ben-Haim et al. |
| 6,645,145 | B1 | 11/2003 | Dreschel et al. |
| 6,845,271 | B2 | 1/2005 | Fang et al. |
| 6,918,871 | B2 | 7/2005 | Schulze |
| 6,947,792 | B2 | 9/2005 | Ben-Haim et al. |
| 7,006,871 | B1 | 2/2006 | Darvish et al. |
| 7,044,921 | B2 | 5/2006 | Asmus et al. |
| 7,071,194 | B2 | 7/2006 | Teng |
| 7,107,092 | B2 | 9/2006 | Goldstein et al. |
| 7,120,497 | B2 | 10/2006 | Ben-Haim et al. |
| 7,155,278 | B2 | 12/2006 | King et al. |
| 7,165,551 | B2 | 1/2007 | Edwards et al. |
| 7,195,881 | B2 | 3/2007 | Geffard |
| 7,206,636 | B1 | 4/2007 | Turcott |
| 7,207,946 | B2 | 4/2007 | Sirokman |
| 7,221,978 | B2 | 5/2007 | Ben-Haim et al. |
| 7,329,489 | B2 | 2/2008 | Kaddurah-Daouk et al. |
| 2001/0025177 | A1 | 9/2001 | Woloszko et al. |
| 2001/0049497 | A1 | 12/2001 | Kalloo et al. |
| 2002/0103424 | A1 | 8/2002 | Swoyer et al. |
| 2003/0040785 | A1 | 2/2003 | Maschino et al. |
| 2003/0148404 | A1 | 8/2003 | Michaelson |
| 2003/0171672 | A1 | 9/2003 | Varghese et al. |
| 2003/0175832 | A1 | 9/2003 | Marton et al. |
| 2003/0195600 | A1 | 10/2003 | Tronnes et al. |
| 2004/0044377 | A1 | 3/2004 | Larsson |
| 2004/0064069 | A1 | 4/2004 | Reynolds et al. |
| 2004/0122360 | A1 | 6/2004 | Waldhauser et al. |
| 2004/0167437 | A1 | 8/2004 | Sharrow et al. |
| 2004/0167442 | A1 | 8/2004 | Shireman et al. |
| 2004/0167443 | A1 | 8/2004 | Shireman et al. |
| 2004/0172090 | A1 * | 9/2004 | Janzig et al. .................. 607/45 |
| 2004/0177388 | A1 | 9/2004 | Botas et al. |
| 2004/0254572 | A1 | 12/2004 | McIntyre et al. |
| 2004/0260198 | A1 | 12/2004 | Rothberg et al. |
| 2004/0260245 | A1 | 12/2004 | Clem et al. |
| 2004/0260246 | A1 | 12/2004 | Desmond |
| 2004/0260337 | A1 | 12/2004 | Freed |
| 2005/0085865 | A1 | 4/2005 | Tehrani |
| 2005/0085866 | A1 | 4/2005 | Tehrani |
| 2005/0085867 | A1 | 4/2005 | Tehrani et al. |
| 2005/0085868 | A1 | 4/2005 | Tehrani et al. |
| 2005/0085869 | A1 | 4/2005 | Tehrani et al. |
| 2005/0107812 | A1 | 5/2005 | Starksen et al. |
| 2005/0107860 | A1 | 5/2005 | Ignagni et al. |
| 2005/0148818 | A1 | 7/2005 | Mesallum |
| 2005/0240241 | A1 | 10/2005 | Yun et al. |
| 2006/0035849 | A1 | 2/2006 | Spiegelman et al. |
| 2006/0041022 | A1 | 2/2006 | Pasinetti |
| 2006/0155222 | A1 | 7/2006 | Sherman et al. |
| 2006/0160087 | A1 | 7/2006 | McGrath et al. |
| 2006/0224209 | A1 | 10/2006 | Meyer |
| 2006/0258667 | A1 | 11/2006 | Teng |
| 2006/0287679 | A1 | 12/2006 | Stone |
| 2007/0038127 | A1 | 2/2007 | Goldstein et al. |
| 2007/0049793 | A1 | 3/2007 | Ignagni et al. |
| 2007/0078099 | A1 | 4/2007 | McLaurin |
| 2007/0117772 | A1 | 5/2007 | Bennett et al. |
| 2007/0150023 | A1 | 6/2007 | Ignagni et al. |
| 2007/0172820 | A1 | 7/2007 | Kaddurah-Daouk et al. |
| 2007/0265611 | A1 | 11/2007 | Ignagni et al. |
| 2007/0274992 | A1 | 11/2007 | Michalovich et al. |
| 2009/0118785 | A1 | 5/2009 | Ignagni et al. |

OTHER PUBLICATIONS

Peterson et al. "Intramuscular Electrical Activation of the Phrenic Nerve." IEEE Transactions on Biomedical Engineering; vol. BME-33, N. 3; Mar. 1986.*

Polkey et al. "Influence of acute lung volume change on contractile properties of human diaphragm." Journal of Applied Physiology Oct. 1998; 85(4): 1316-1321.*

Sarnoff et al. "Electrophrenic Respiration." Science Oct. 29, 1948; 108: 482.*

Ayas, N. T.; Prevention of Human Diaphragm Atrophy with Short Periods of Electrical Stimulation; Am J Respir Crit Care Med; vol. 159. pp. 2018-2020, 1999.

Schmit, Brian D. et al.; Laparoscopic Placement of Electrodes for Diaphragm Pacing Using Stimulation to Locate the Phrenic Nerve Motor Points; IEEE; vol. 6 No. 4; Dec. 1998.

"Diaphragm Activation with Intramuscular Stimulation in Dogs"; M.L. Nochomozitz, et al.; American Review of Respiratory Disease, vol. 127 N. 3; Mar. 1983.

"Conditioning of the Diaphragm with Phrenic Nerve Stimulation after Prolonged Disuse"; M.L. Nochomozitz, et al.; American Review of Respiratory Disease, vol. 130 N. 4; Oct. 1984.

"Intramuscular Electrical Activation of the Phrenic Nerve"; D.K. Peterson, et al.; IEEE Transactions on Biomedical Engineering; vol. BME-33, N. 3; Mar. 1986.

"Electrical Activation of Respiratory Muscles by Methods Other than Phrenic Nerve Cuff Electrodes"; D.K. Peterson, et al.; Pacing and Clinical Electrophysiology; vol. 12, No. 5, pp. 749-878; May 1989.

"Mapping the Phrenic Nerve Motor Point: The Key to a Successful Laparoscopic Diaphragm Pacing System in the First Human Series"; R. Onders, et al.; Surgery; vol. 136, No. 4; Oct. 2004.

"Restoration of Respiratory Muscle Function Following Spinal Cord Injury Review of Electrical and Magnetic Stimulation Techniques"; A.F. DiMarco; Respiratory Physiology & Neurobiology 147 (2005).

Onders et al.; U.S. Appl. No. 12/122,482 entitled "Devices and methods for assessing motor point electromyogram as a biomarker," filed May 16, 2008.

DeCarvalho et al.; Motor neuron disease presenting with respiratory failure; Journal of the Neurological Sciences; vol. 139; No. Suppl.; 1996; pp. 117-122.

Stewart et al.; Electromyography of respiratory muscles in amyotrophic lateral sclerosis; Journal of the Neurological Sciences; vol. 191; No. 1-2; Oct. 15, 2001; pp. 67-73.

Ignagni et al; U.S. Appl. No. 11/716,475 entitled "Ventilatory assist system and methods to improve respiratory function," filed Mar. 9, 2007.

Ignagni et al; U.S. Appl. No. 11/467,025 entitled "Method and apparatus for grasping an abdominal wall," filed Aug. 24, 2006.

Ignagni et al; U.S. Appl. No. 12/026,428 entitled "Intramuscular electrode," filed Feb. 5, 2008.

Knutson et al.; Electrode fracture rates and occurrences of infection and granuloma associated with percutaneous intramuscular electrodes in upper-limb functional electrical stimulation applications; Journal of Rehabilitation Research and Development; vol. 39; No. 6; pp. 671-684, Nov./Dec. 2002.

Peterson et al.; Long-term intramuscular electrical activation of the phrenic nerve: Safety and reliability; IEEE; vol. 41; No. 12; pp. 1115-1126; Dec. 1994.

* cited by examiner

SYSTEM AND METHOD FOR CONDITIONING A DIAPHRAGM OF A PATIENT

CROSS REFERENCE TO RELATED APPLICATION

The present application claims priority to U.S. Provisional Patent Application No. 60/481,124 filed on Jul. 23, 2003, which is herein incorporated by reference in its entirety.

BACKGROUND

A patient may need respiratory assistance as a result of disease and injuries of various kinds. The need can be direct, especially when the injury or illness afflicts the patient's respiratory system. The need can also be indirect, e.g. during anaesthesia and some intensive care. The respiratory assistance can encompass everything from facilitating spontaneous breathing to total control of breathing. Typically, a mechanical ventilator is employed to provide the breathing assistance.

One potential problem occurring in long-term controlled respiration is that the patient's own respiratory musculature becomes weakened. In many instances, the patient then loses the ability to breathe spontaneously after the true need for assisted respiration has been eliminated. Weaning the patient off the ventilator then takes longer. This causes a cost increase to the society in the form of longer treatment duration times and, more important, increases the discomfort and risk of secondary disease for the patient.

Amyotrophic Lateral Sclerosis (ALS, also known as Lou Gehrig's Disease or Motor Neuron Disease) is a progressive neurodegenerative disease of unknown cause. Approximately 1.4 individuals per 100,000 develop ALS annually and the peak incidence is between the ages of 55 and 75. The exact etiology of ALS is unknown although many potential causes have been proposed including exposure to neurotoxic agents, genetic or autoimmune disease, deficiencies of nerve growth factors, and viral infection. The typical clinical presentation is that of an individual with gradually progressive asymmetric weakness associated with hyperreflexia, muscle atrophy and fasciculations. Typically patients have difficulty with walking, balance, picking up objects, and eventually any limb muscle movement. The diagnosis of ALS is made on the basis of the history, a physical examination revealing upper and lower motor neuron signs, and electromyography demonstrating signs of disseminated active denervation and true reinnervation.

One effect of progressive neuromuscular weakness in patients with ALS is the effect on respiration. Although ALS has no direct effect on the lung, it has devastating effects on mechanical function of the respiratory system. ALS affects all of the major respiratory muscle groups: upper airway muscles, expiratory muscles, and inspiratory muscles. Therefore, all patients with ALS are at significant risk for respiratory complications. Progressive inspiratory muscle weakness in ALS inevitably leads to carbon dioxide retention, inability to clear secretions and hypercarbic respiratory failure, the major cause of death in ALS. At some point, ALS involves the respiratory muscles so severely that bulbar paresis is combined with severe expiratory and inspiratory muscle weakness and invasive ventilation becomes the only option for survival.

BRIEF DESCRIPTION OF THE DRAWINGS

It will be appreciated that illustrated boundaries of elements (e.g. boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa.

DETAILED DESCRIPTION OF ILLUSTRATED EMBODIMENTS

Figure 1:
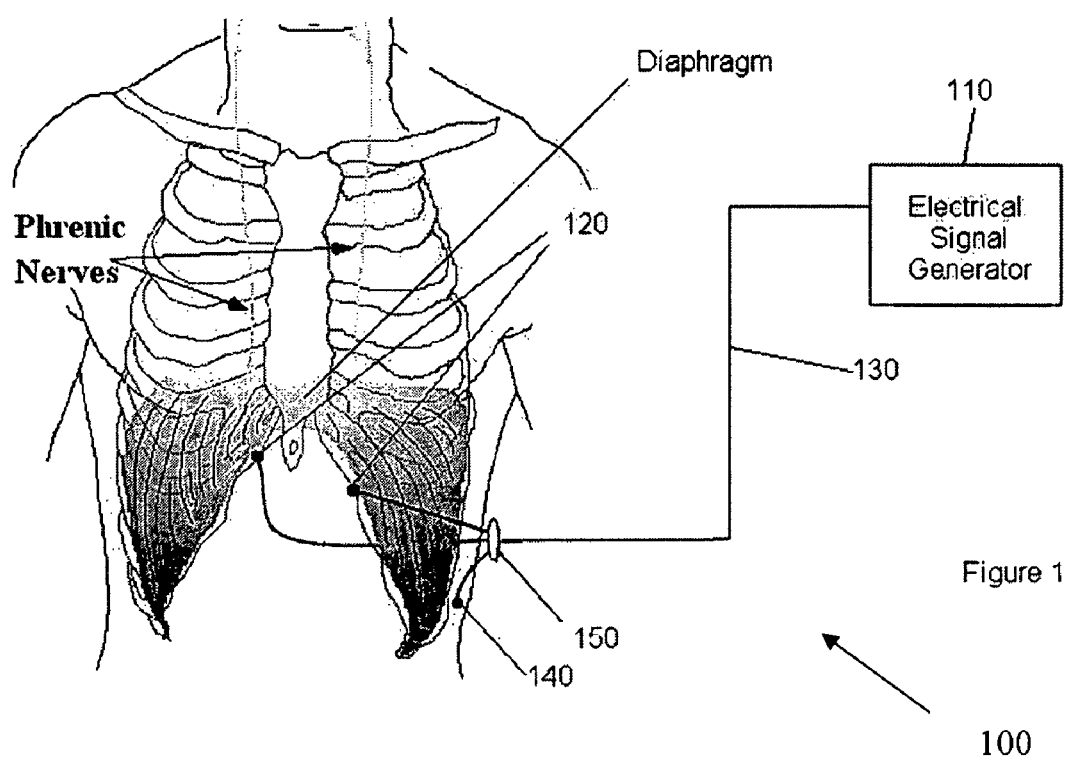
FIG. 1 is a schematic diagram of one embodiment of a system 100 for conditioning a diaphragm of a patient.

The following includes definitions of selected terms used throughout the disclosure. The definitions include examples of various embodiments and/or forms of components that fall within the scope of a term and that may be used for implementation. Of course, the examples are not intended to be limiting and other embodiments may be implemented. Both singular and plural forms of all terms fall within each meaning:

"Patient," as used herein, includes but is not limited to any living creature, i.e. human or animal.

"Signal", as used herein, includes but is not limited to one or more electrical signals, AC or DC, analog or digital signals, one or more computer or processor instructions, or other means that can be received, transmitted, and/or detected.

"Software", as used herein, includes but is not limited to one or more computer readable and/or executable instructions that cause a computer or other electronic device to perform functions, actions, and/or behave in a desired manner. The instructions may be embodied in various forms such as objects, routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software may be dependent on, for example, requirements of a desired application, the environment it runs on, and/or the desires of a designer/programmer or the like. It will also be appreciated that computer-readable and/or executable instructions can be located in one logic and/or distributed between two or more communicating, co-operating, and/or parallel processing logics and thus can be loaded and/or executed in serial, parallel, massively parallel and other manners.

A system and method is provided for electrically stimulating the diaphragm of a patient to condition the diaphragm of the patient. As used herein, the term "condition" can mean maintaining the strength of, strengthening, building the fatigue resistance of the diaphragm of the patient, or changing other contractile properties of the diaphragm muscle fibers. Although not wishing to be bound by theory, electrical stimulation can also have one or more of the following effects that are intended to be included in the meaning of the term "condition": 1) eliciting muscle fiber type conversion (from fast twitch, rapidly fatiguing, type I fibers to slow twitch, slowly fatiguing type II fibers); 2) increasing muscle mass (through reversal of disuse atrophy); 3) changing the contractile properties of the muscle by stimulating through the muscle's range of motion (thereby reducing any shortening of fibers and/or spasticity), and 4) even potentially having an effect of collateral sprouting of adjacent nerve fibers to innervate muscle that has lost its innervation through damage to the phrenic nerve or lower motor neuron.

To condition the diaphragm of the patient, a sufficient amount of electrical stimulation can be continuously or periodically applied to one or more sites in the diaphragm to achieve at least one of the effects described above.

Illustrated in FIG. 1 is one embodiment of a system 100 for electrically stimulating the diaphragm of a patient to condition the diaphragm of the patient. The system 100 can be used to treat patients having ALS or any other disorder that attacks the respiratory musculature. Generally, the system 100 can include an electrical signal generator 110, electrodes 120 implanted into the diaphragm of the patient to apply electrical stimulation to the diaphragm of the patient. Electrical signal generator 110 is connected to electrodes 120 by stimulus cable 130 and a percutaneous connector 150 as shown.

In one embodiment, the electrical signal generator 110 can be configured to generate pulses and/or signals that may take the form of sinusoidal, stepped, trapezoidal waveforms or other relatively continuous signals. The electric signal generator 110 can include one or more channels that can independently control the amplitude, frequency, timing and pulse width of the corresponding electrodes connected thereto.

In one embodiment, the electrical signal generator 110 can be an external signal generator that is electrically connected to or in electrical communication with the electrodes 120. One example of a suitable electrical signal generator is the NeuRx RA/4 stimulator that is manufactured by Synapse Biomedical, Inc. of Oberlin, Ohio. The NeuRx RA/4 stimulator is a four-channel device with independent parameter programmability. It will be appreciated that since the NeuRx RA/4 stimulator has four channels, it has the capability to independently control up to four electrodes. In an alternative embodiment, the electrical signal generator 110 can be an implantable signal generator. One suitable example of a fully implanted signal generator is the "ITREL II" electrical signal generator available from Medtronic, Inc. of Minneapolis, Minn. One example of a partially implanted radio-frequency signal generator system is the "XTREL" system also available from Medtronic, Inc.

As stated above, the system 100 can include electrodes 120 implanted in the diaphragm of the patient to provide electrical stimulation to the diaphragm. Although FIG. 1 illustrates utilization of two electrodes in the system 100, it will be appreciated that more than two electrodes or one electrode can be used to provide sufficient electrical stimulation.

Figure 2:
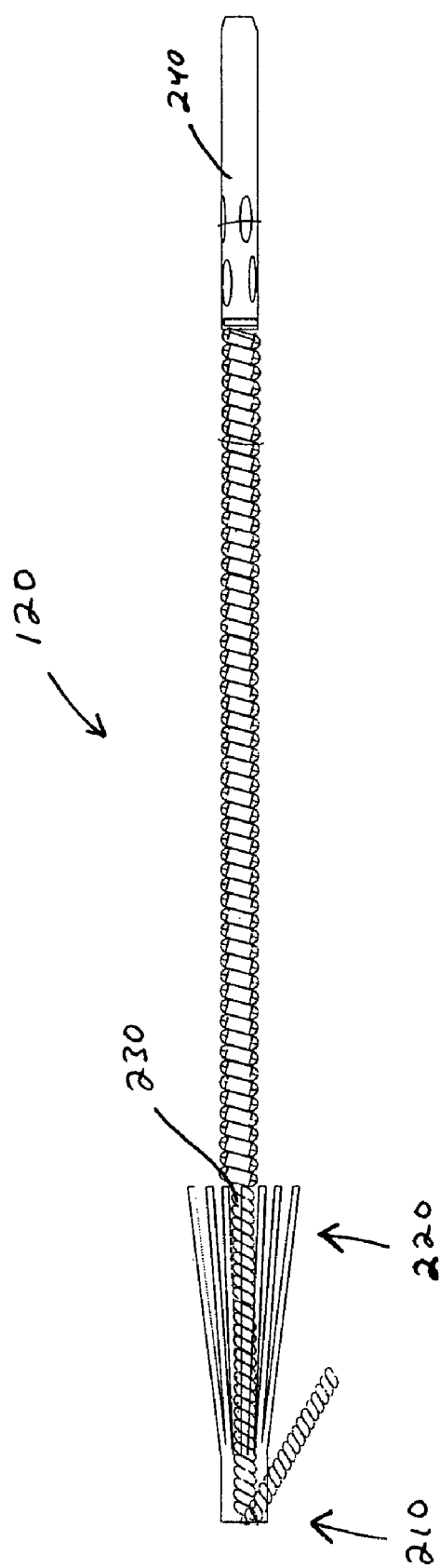
FIG. 2 is a plan view of one embodiment of an intramuscular electrode.

Illustrated in FIG. 2 is one embodiment of an intramuscular electrode 120 that can be implanted into a patient. For example, the electrode 120 can be an intramuscular electrode that is configured to be implanted into the muscle tissue of the patient. In one embodiment, the intramuscular electrode 120 can serve as a cathode.

One example of a suitable intramuscular electrode is the Peterson intramuscular electrode (P/N 21-0002) manufactured by Synapse Biomedical, Inc. of Oberlin, Ohio, which is the electrode illustrated in FIG. 2. In one configuration, the Peterson intramuscular electrode is a double helix wound from multistrand stainless steel wire insulated in fluoropolymer with a polypropylene core and barb. The electrode can have a barb 210 that is flattened and bent back along the line of the electrode, a polypropylene skirt 220, and a deinsulated coil 230 under the skirt 220. The electrode lead can terminate with a stainless steel pin 240 crimped to the de-insulated end and back-filled with silicone adhesive for strain relief. Obviously, it will be appreciated that the intramuscular electrode can take the form of other shapes, sizes, and configurations, and can be made of other materials suitable for implantation into a patient.

In one embodiment, the electrodes 120 can be implanted into target sites in the diaphragm of the patient. For example, the electrodes 120 can be implanted into or adjacent the phrenic nerve motor points of the diaphragm (i.e., where the phrenic nerve enters the diaphragm) of the patient. The phrenic nerve motor points of the diaphragm are locations in the diaphragm that provide the greatest muscle fiber recruitment in response to an applied stimulation.

Figure 3:
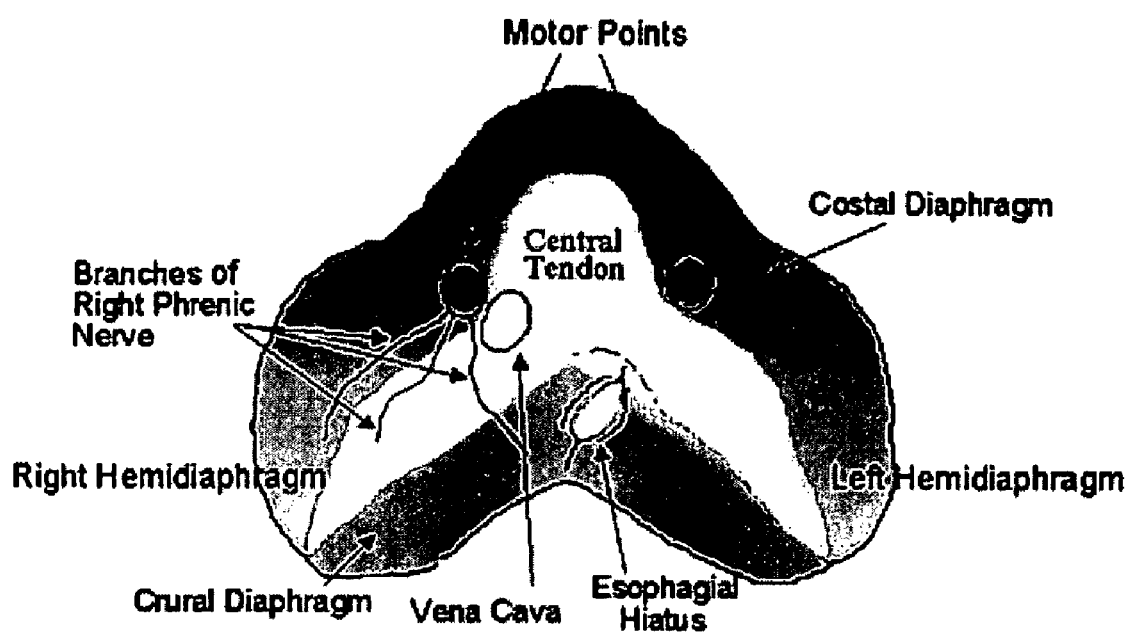
FIG. 3 is a diagram of the anatomy of the diaphragm from the view point of the abdominal surface.

Illustrated in FIG. 3 is a cross-section of an exemplary diaphragm and the locations of the motor points in each hemidiaphragm. The phrenic nerve motor points of the diaphragm can be advantageous sites to implant the electrodes because electrical stimulation of these sites can produce a diaphragmatic contraction. It will be appreciated that the diaphragm can be defined in terms of left and right hemidiaphragms and that one or more electrodes can be implanted into or adjacent the phrenic nerve motor points of only the left hemidiaphragm, only the right hemidiaphragm, or both left and right hemidiaphragm.

In one embodiment, an electrode 120 can be implanted into or adjacent the phrenic nerve motor points of each hemidiaphragm and an additional electrode can be implanted in each hemidiaphragm for one or more of the following reasons: 1) to backup the primary electrode (i.e., the electrode implanted adjacent the phrenic nerve motor point); 2) to be positioned near the primary electrode to gain higher output if the phrenic nerve motor point is imprecisely located; or 3) to be positioned near the primary electrode to allow for surgical error in placement near the phrenic nerve motor point. Alternatively, if the phrenic nerve motor point is on the central tendon, one or more electrodes can be positioned near branches of the phrenic nerve.

In one embodiment, the system 100 can include an indifferent electrode 140. The indifferent electrode 140 can be similar to the intramuscular electrodes 120 shown and described above, except that it has a shorter de-insulated tip and does not have a barb at one end. In one embodiment, the indifferent electrode can be used as a common anode that can provide a return for the electrical charge from the electrodes 120. One suitable example of an indifferent electrode is PN 21-0004 manufactured by Synapse Biomedical, Inc. It will be appreciated that other indifferent electrodes can take the form of other shapes, sizes, and configurations, and can be made of other materials suitable for implantation into a patient or placed on the skin surface.

In one embodiment, the indifferent electrode 140 can be implanted in the subcutaneous tissue adjacent the diaphragm of the patient. Alternatively, the indifferent electrode 140 can be implanted in other areas such as integral to an implanted pulse generator or placed on the skin surface.

In one embodiment, the electric signal generator 110 can supply the electrodes 120 with an electrical signal that serves as electrical stimulation. For example, the electrical signal can be a capacitively coupled, charge balanced, biphasic, constant current waveform with adjustable parameters as shown below in Table I. It will be appreciated that the electrical signal can take the form of other waveforms for electrical stimulation such as monophasic or rectangular biphasic.

TABLE I

| Parameter | Range |
| --- | --- |
| Stimulation Interleave Rate | 1-100 |
| Trigger Delay (from inspiration) | 1.0-4.0 s |
| Stimulation Time | 0.8-1.5 s |
| Output Pulse Period | 20-250 ms |
| Pulse Width Modulation Count | 0-10 |
| Cathodic Current Amplitude | 5-25 mA |
| Cathodic Current Pulse Width | 20-200 μs |
| Voltage | 0-65 V |
| Pulse Frequency | 10-20 Hz |

In one embodiment, the electrical stimulation can be delivered to the diaphragm of the patient continuously or periodically. For example, the electrical stimulation can be delivered to the diaphragm of the patient at specified intervals per day (e.g. 5-6 sessions per day) for a certain period of time per interval (e.g. 5 minutes per session totaling about 25-30 minutes per day). Obviously, the electrical stimulation can be delivered at different intervals depending on the needs of a particular patient.

In one embodiment, the electrodes 120 can be implanted into the diaphragm of the patient using a laproscopic procedure. One suitable device that can be used to implant the electrodes 120 into the patient's diaphragm is the electrode delivery instrument shown and described in U.S. Pat. No. 5,797,923, which is herein incorporated by reference in its entirety. In another embodiment, the electrodes 120 can be implanted into the diaphragm of the patient using an open surgical technique and placement with a hypodermic needle.

To locate the phrenic nerve motor points in each hemidiaphragm of the patient, a mapping procedure can be performed on the patient. In one mapping procedure, a test electrode and mapping software can be used to map the response of stimulus in each hemidiaphragm. The electrode includes a metal ring surrounded by tubing. The tubing extends from the metal ring a surgery-room vacuum port. The tubing is also connected to a pressure transducer for measurement of intra-abdominal pressure during the mapping procedure. To begin the procedure, the electrode is placed into contact with the diaphragm muscle tissue and held against the muscle tissue with suction. When the electrode is introduced into the peritoneal space, the tubing and metal ring are enclosed within a cannula. When a desired test site has been identified, a standard laparoscopic dissector is used to position and temporarily hold the electrode against the muscle tissue until the suction has been turned on. Electrical stimulation (e.g., stimulus amplitude of 20 mA and pulse duration of 100 μs) is delivered through the electrode resulting in diaphragm contraction. The magnitude of the evoked muscle response and visual confirmation of the contraction are recorded and noted, respectively. Also, the resultant change in pressure of the abdominal cavity is recorded. The suction can then be turned off, the electrode moved to a new test site, and the process can be repeated. With this information, the diaphragm of the patient is methodically mapped on a grid pattern (e.g., overlayed on the laparoscopic monitor).

The magnitude of the evoked muscle response and the resultant change in pressure of the abdominal cavity can then be used to identify the optimal electrode implant site of each hemidiaphragm. The optimal site, which is typically referred to as a phrenic nerve motor point of the hemidiaphragm, is chosen as the site that elicits a diffuse contraction and the greatest magnitude of pressure change. Although one mapping procedure has been described in detail above, it will be appreciated that other mapping procedures can be used to identify the phrenic nerve motor points in the diaphragm of the patient. For example, another suitable mapping procedure and device is shown and described in U.S. Patent Application entitled "Minimally Invasive Surgical Stimulation Tool" filed on the same date herewith, which is herein incorporated by reference in its entirety.

Figure 4:
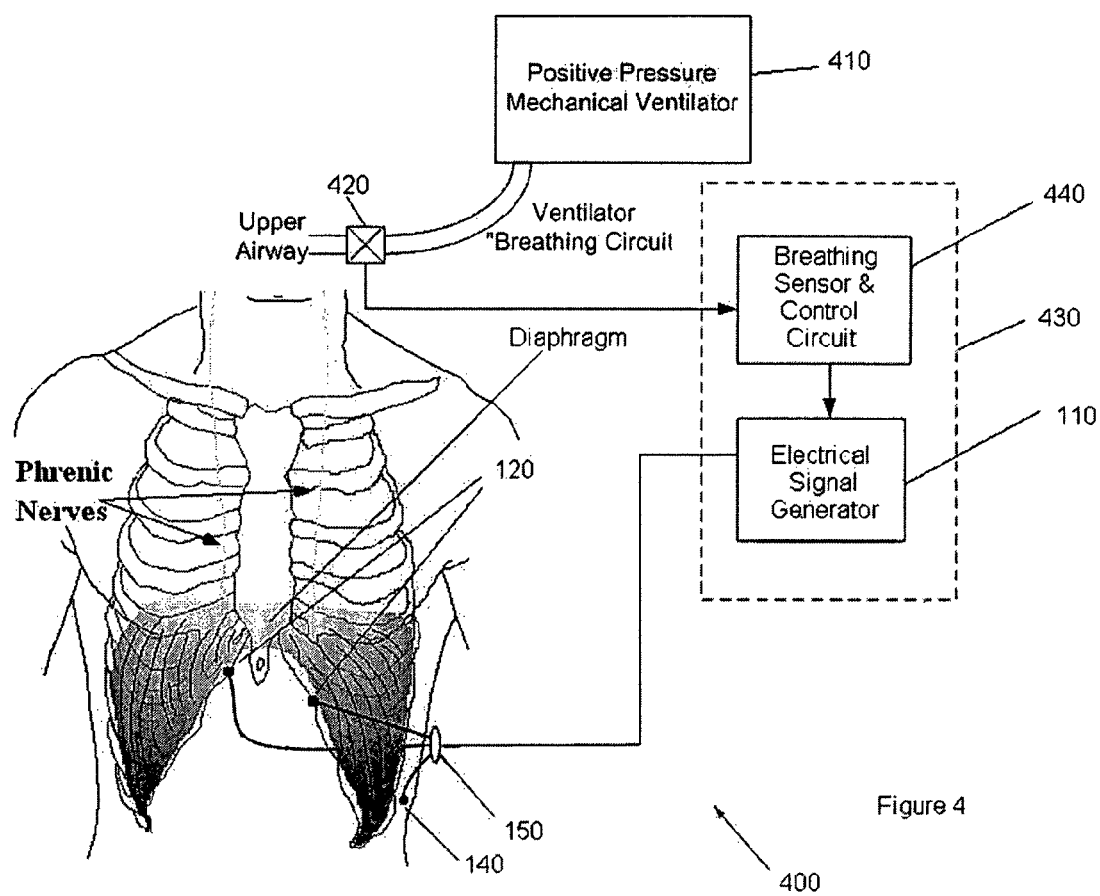
FIG. 4 is a schematic diagram of another embodiment of a system 400 for conditioning a diaphragm of a patient.

Illustrated in FIG. 4 is another embodiment of a system 400 for conditioning the diaphragm of a patient. The system 400 is similar to the system 100 shown in FIG. 1 and described above, except that the system 400 is used in conjunction with a mechanical ventilator 410. The system 400 can be applicable to patients with acute ventilatory needs by providing mechanical ventilation to the patient along with diaphragm electrical stimulation to condition the diaphragm of the patient. In such system, the mechanical ventilator would provide the gas exchange required for patient support, while the diaphragm electrical stimulation could be used to condition the diaphragm.

In one embodiment, the system 400 can further include a flow sensor 420 provided along the ventilation breathing circuit (i.e., between the mechanical ventilator 410 and the upper airway of the patient). The flow sensor 420 can be used to sense inspiratory or expiratory air flow in the ventilator circuit.

In one embodiment, the system 400 can include a stimulation apparatus 430 that can include an electrical signal generator 110 (similar to the one described above) and a breathing sensor and control circuit 440 that is in electrical communication with the electrical signal generator 110 and the flow sensor 420. The breathing sensor and control circuit 440 can be configured to detect certain breathing attributes of the patient (e.g., the inspiration phase of a breath, the duration of the inspiration phase, the exhalation phase of a breath, the duration of the exhalation phase, tidal volume, and/or flow rate), convert these attributes to signals, and communicate these signals to the electrical signal generator 110.

Optionally, the system 400 can include a pressure gauge (not shown) and gas meter (not shown). These can be provided along the ventilator breathing circuit to measure the pressure and gas-related parameters of the patient's breathing, respectively. Also, a physiological measurement unit can be connected to the patient to measure certain physiological parameters such as blood pressure, blood values, body temperature, etc.

In one embodiment, electrical stimulation of the diaphragm can be synchronized with attempts at breathing or breathing made by the patient (e.g., on the patient's own or by the mechanical ventilator). For example, electrical stimulation can be triggered following the inspiration phase of the breath (i.e., during exhalation) to maximize the contraction during the period when the diaphragm is at its longest length. This could be beneficial to a patient with injuries to or blockages in her/his nerve conduction system between the respiratory center and the respiratory musculature. It will be appreciated that electrical stimulation of the diaphragm of the patient may not be synchronized with attempts at breathing or breathing made by the patient and, thus, can be applied during any portion of a breath.

By applying electrical stimulation to the diaphragm periodically or at specified intervals, weakening of the diaphragm can be reduced. When the condition of the patient improves and he/she makes sporadic attempts to breathe naturally, adaptation to these attempts can be made in combination with intensified muscle stimulation. This can increase exercise of the diaphragm and prepare the patient for the time when the patient starts taking over an increasing part of the breathing.

One possible advantage of periodically delivering electrical stimulation to the patient's diaphragm to condition the diaphragm of the patient while the patient is using a mechanical ventilator is that the dependence of the patient on the mechanical ventilator can end sooner. For example, electrical stimulation of the diaphragm while the patient is breathing using a mechanical ventilator can help wean the patient off the mechanical ventilator by reversing the disuse atrophy of the diaphragm, thereby providing fatigue resistance and strength. Initially, patients may only be able to tolerate electrical stimulation of the diaphragm for a short period of time due to rapid muscle fatigue and low diaphragm strength resulting in low tidal volumes. Over a period of weeks, the diaphragm can build endurance and strength and patients may be able to tolerate electrical stimulation of the diaphragm for longer durations until they are able to achieve full-time electrical stimulation. This can mean that the duration of hospital treatment can be greatly reduced. Moreover, it may be possible to reduce costs and treat more patients at hospitals when treatment durations are reduced.

Figure 5:
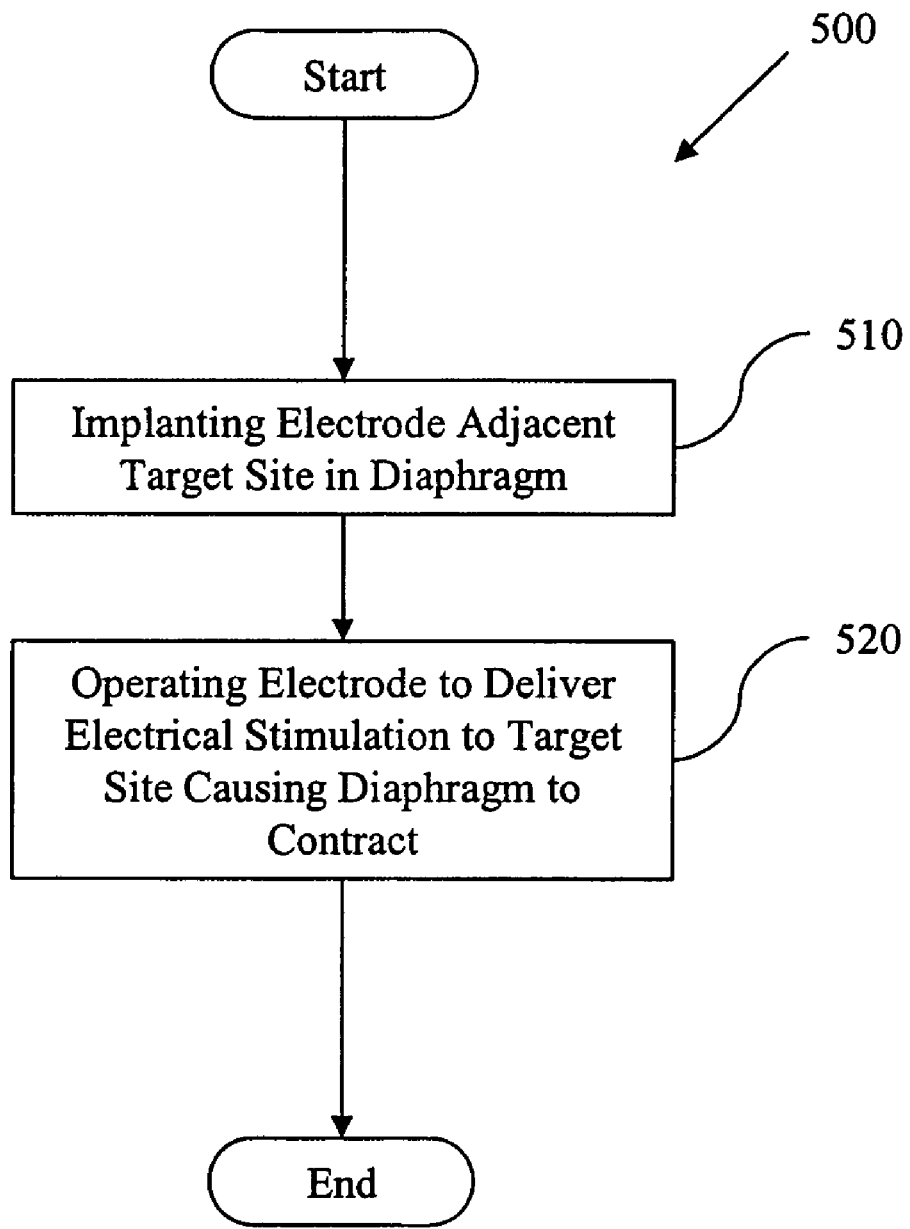
FIG. 5 is a schematic diagram of one embodiment of a methodology 500 for conditioning the diaphragm of a patient.

Illustrated in FIG. 5 is one embodiment of a methodology 500 associated with conditioning the diaphragm of a patient. The illustrated elements denote "processing blocks" and represent computer software instructions or groups of instructions that cause a computer or processor to perform an action (s) and/or to make decisions. Alternatively, the processing blocks may represent functions and/or actions performed by functionally equivalent circuits such as an analog circuit, a digital signal processor circuit, an application specific integrated circuit (ASIC), or other logic device. The diagram, as well as the other illustrated diagrams, does not depict syntax of any particular programming language. Rather, the diagram illustrates functional information one skilled in the art could use to fabricate circuits, generate computer software, or use a combination of hardware and software to perform the illustrated processing. It will be appreciated that electronic and software applications may involve dynamic and flexible processes such that the illustrated blocks can be performed in other sequences different than the one shown and/or blocks may be combined or, separated into multiple components. They may also be implemented using various programming approaches such as machine language, procedural, object oriented and/or artificial intelligence techniques. The foregoing applies to all methodologies described herein.

As shown in FIG. 5, the method 500 includes implanting an electrode adjacent a target site in the diaphragm of the patient (block 510). Once the electrode has been implanted, the electrode can be operated to deliver a sufficient amount of electrical stimulation to the target site in the diaphragm of the patient to cause the diaphragm to contract (block 520). The electrical stimulation can be delivered periodically to cause periodic contractions of the diaphragm and thereby condition the diaphragm.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicant's general inventive concept.

What is claimed is:

1. A method of treating a neurodegenerative disorder of a patient affecting the patient's diaphragm, the method comprising the steps of:
   identifying the patient as having a neurodegenerative disorder;
   delivering electrical stimulation to a target site in the diaphragm through an electrode implanted in the diaphragm to contract the diaphragm; and
   synchronizing the delivering step with a breath or breathing attempt made by the patient to condition the diaphragm.

2. The method of claim 1 further comprising implanting the electrode adjacent the target site.

3. The method of claim 2, further comprising the step of:
   identifying the target site in the diaphragm of the patient prior to the implanting step.

4. The method of claim 1, wherein the target site of the diaphragm is the phrenic nerve motor point of a hemidiaphragm of the patient.

5. The method of claim 4 further comprising delivering electrical stimulation to a phrenic nerve motor point in another hemidiaphragm of the patient through a second electrode implanted in the other hemidiaphragm.

6. The method of claim 1 wherein the electrical stimulation is delivered at specified intervals.

7. The method of claim 1 wherein the electrical stimulation has a pulse frequency between about 5 Hz and about 50 Hz.

8. The method of claim 1 wherein the electrical stimulation has a pulse width between about 20 μs and about 200 μs.

9. The method of claim 1 wherein the electrical stimulation has a pulse amplitude between about 5 mA and about 25 mA.

10. The method of claim 1 further comprising the step of:
    delivering breathing gas to the patient from a ventilator to assist breathing by the patient at specified gas delivery intervals.

11. The method of claim 10 further comprising the step of:
    synchronizing delivery of the breathing gas to the patient by the ventilator with delivery of the electrical stimulation of the target site in the diaphragm of the patient by the electrode.

12. The method of claim 11 wherein electrical stimulation can be delivered to the target site of the diaphragm following the inspiration phase of a breath by the patient.

13. The method of claim 1 wherein the electrical stimulation provides a sufficient number, duration, and range of diaphragm contractions to elicit a change in strength, fatigue resistance, or fiber contractile properties.

14. The method of claim 1 wherein the neurodegenerative disease is amyotrophic lateral sclerosis.

* * * * *